(12) United States Patent
Bonutti

(10) Patent No.: US 8,251,934 B2
(45) Date of Patent: *Aug. 28, 2012

(54) ORTHOSIS AND METHOD FOR CERVICAL MOBILIZATION

(75) Inventor: Peter M. Bonutti, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 154 days.

This patent is subject to a terminal disclaimer.

(21) Appl. No.: 11/953,145

(22) Filed: Dec. 10, 2007

(65) Prior Publication Data

US 2008/0091132 A1    Apr. 17, 2008

Related U.S. Application Data

(63) Continuation of application No. 10/909,584, filed on Aug. 2, 2004, now Pat. No. 7,306,573, which is a continuation of application No. 10/329,866, filed on Dec. 26, 2002, now Pat. No. 6,770,047, which is a continuation of application No. 09/728,106, filed on Dec. 1, 2000, now Pat. No. 6,503,213.

(51) Int. Cl.
  *A61F 5/00* (2006.01)
(52) U.S. Cl. .............. 602/18; 602/19; 602/32
(58) Field of Classification Search ............. 602/17–19, 602/32–36; 128/DIG. 23
  See application file for complete search history.

(56) References Cited

U.S. PATENT DOCUMENTS

| | | | |
|---|---|---|---|
| 432,327 A | 7/1890 | Page | |
| 433,227 A | 7/1890 | Beacock | |
| 2,191,283 A | 2/1940 | Longfellow | |
| 2,206,902 A | 7/1940 | Kost | |
| 2,223,276 A * | 11/1940 | Ward | 602/18 |
| 2,237,252 A | 4/1941 | Longfellow | |
| 2,246,689 A | 6/1941 | Kost | |
| 2,250,493 A | 7/1941 | Milne | |
| 2,590,729 A | 3/1952 | Scognamillo | |
| 2,590,739 A | 3/1952 | Wahner et al. | |
| 2,642,864 A * | 6/1953 | Ward | 602/36 |
| 2,811,154 A | 10/1957 | Scholl | |
| 2,820,455 A * | 1/1958 | Hall | 602/18 |

(Continued)

FOREIGN PATENT DOCUMENTS

CA    2066151    10/1992

(Continued)

OTHER PUBLICATIONS

Advertising materials from the Internet on Jun. 5, 1998 entitled: "Quadrant by Smith & Nephew DonJoy". "Entering a New Plane".

(Continued)

*Primary Examiner* — Michael A. Brown
(74) *Attorney, Agent, or Firm* — Armstrong Teasdale LLP

(57) ABSTRACT

A method of using a neck brace to move a neck of a person or stabilize the neck includes connecting a vest of the neck brace to a torso of a person. A support member of the neck brace is connected to the vest. A chin support of the neck brace is connected to a chin of the person. Force is applied between the support member and the chin support to move the chin support relative to the support member. A cam member of the neck brace guides movement of the chin support relative to the support member.

56 Claims, 6 Drawing Sheets

U.S. PATENT DOCUMENTS

| | | | |
|---|---|---|---|
| 2,829,562 A | 4/1958 | La Rue | |
| 2,832,334 A | 4/1958 | Whitelaw | |
| 3,083,708 A | 4/1963 | Gottfried | |
| 3,338,237 A | 8/1967 | Sconce | |
| 3,351,055 A | 11/1967 | Gottfried | |
| 3,548,818 A | 12/1970 | Kaplan | |
| 3,580,248 A | 5/1971 | Larson | |
| 3,698,389 A | 10/1972 | Guedel | |
| 3,701,349 A | 10/1972 | Larson | |
| 3,724,452 A * | 4/1973 | Nitschke | 602/18 |
| 3,760,056 A | 9/1973 | Rudy | |
| 3,795,243 A * | 3/1974 | Miller | 602/36 |
| 3,811,434 A | 5/1974 | Jacobson et al. | |
| 3,814,419 A | 6/1974 | Bjorklund et al. | |
| 3,856,004 A | 12/1974 | Cox | |
| 3,915,161 A * | 10/1975 | Shields | 602/36 |
| 3,955,565 A | 5/1976 | Johnson, Jr. | |
| 3,970,316 A | 7/1976 | Westmoreland, Jr. | |
| 3,976,057 A | 8/1976 | Barclay | |
| 4,015,597 A * | 4/1977 | Beaver | 602/36 |
| 4,039,183 A | 8/1977 | Sakurada | |
| 4,076,022 A | 2/1978 | Walker | |
| 4,084,267 A | 4/1978 | Zadina | |
| 4,108,170 A | 8/1978 | Spann | |
| 4,180,870 A | 1/1980 | Radulovic et al. | |
| 4,214,577 A | 7/1980 | Hoy | |
| 4,229,001 A | 10/1980 | Roman | |
| 4,237,873 A | 12/1980 | Terry et al. | |
| 4,241,731 A | 12/1980 | Pauley | |
| 4,273,113 A | 6/1981 | Hofstein | |
| 4,285,773 A | 8/1981 | Taciuk | |
| 4,320,748 A | 3/1982 | Racette et al. | |
| 4,363,481 A | 12/1982 | Erickson | |
| 4,370,977 A | 2/1983 | Mauldin et al. | |
| 4,383,523 A | 5/1983 | Schurman | |
| 4,396,013 A | 8/1983 | Hasslinger | |
| 4,401,111 A | 8/1983 | Blackstone | |
| 4,417,569 A | 11/1983 | Brudny | |
| 4,441,489 A | 4/1984 | Evans et al. | |
| 4,454,871 A | 6/1984 | Mann et al. | |
| 4,456,001 A | 6/1984 | Pescatore | |
| 4,456,002 A | 6/1984 | Barber et al. | |
| 4,502,470 A | 3/1985 | Kiser et al. | |
| 4,502,681 A | 3/1985 | Blomqvist | |
| 4,508,111 A | 4/1985 | Hepburn | |
| 4,509,509 A | 4/1985 | Bouvet et al. | |
| 4,538,595 A | 9/1985 | Hajianpour | |
| 4,538,600 A | 9/1985 | Hepburn | |
| 4,570,619 A | 2/1986 | Gamm | |
| 4,576,151 A | 3/1986 | Carmichael et al. | |
| 4,589,406 A | 5/1986 | Florek | |
| 4,606,542 A | 8/1986 | Segal | |
| 4,612,919 A | 9/1986 | Best | |
| 4,628,913 A | 12/1986 | Lerman | |
| 4,641,639 A | 2/1987 | Padilla | |
| 4,653,479 A | 3/1987 | Maurer | |
| 4,665,905 A | 5/1987 | Brown | |
| 4,693,239 A | 9/1987 | Clover, Jr. | |
| 4,716,889 A | 1/1988 | Saringer | |
| 4,718,665 A | 1/1988 | Airy et al. | |
| 4,727,865 A | 3/1988 | Hill-Byrne | |
| 4,739,334 A | 4/1988 | Soref | |
| 4,765,320 A | 8/1988 | Lindemann et al. | |
| 4,788,941 A | 12/1988 | Villeneuve | |
| 4,790,301 A | 12/1988 | Silfverskiold | |
| 4,793,334 A | 12/1988 | McGuinness et al. | |
| 4,805,601 A | 2/1989 | Eischen, Sr. | |
| 4,807,601 A | 2/1989 | Wright | |
| 4,809,688 A | 3/1989 | Aymerica del Valle et al. | |
| 4,834,073 A | 5/1989 | Bledsoe et al. | |
| 4,844,094 A | 7/1989 | Grim | |
| 4,844,454 A | 7/1989 | Rogers | |
| 4,844,455 A | 7/1989 | Funkhouser, Jr. | |
| 4,848,326 A | 7/1989 | Lonardo | |
| 4,862,877 A | 9/1989 | Barber | |
| 4,865,024 A | 9/1989 | Hensley et al. | |
| 4,869,267 A | 9/1989 | Grim et al. | |
| 4,869,499 A | 9/1989 | Schiraldo | |
| 4,884,454 A | 12/1989 | Johnson | |
| 4,913,135 A * | 4/1990 | Mattingly | 602/18 |
| 4,913,755 A | 4/1990 | Grim | |
| 4,930,497 A | 6/1990 | Saringer | |
| 4,953,543 A | 9/1990 | Grim et al. | |
| 4,955,369 A | 9/1990 | Bledsoe et al. | |
| 4,955,396 A | 9/1990 | Fralick et al. | |
| 4,957,281 A | 9/1990 | Christolear, Jr. | |
| 4,964,402 A | 10/1990 | Grim et al. | |
| 4,991,234 A | 2/1991 | Greenberg | |
| 4,996,979 A | 3/1991 | Grim et al. | |
| 5,005,563 A | 4/1991 | Veale | |
| 5,018,514 A | 5/1991 | Grood et al. | |
| 5,019,050 A | 5/1991 | Lynn et al. | |
| 5,025,782 A | 6/1991 | Salerno | |
| 5,027,688 A | 7/1991 | Suzuki et al. | |
| 5,027,801 A | 7/1991 | Grim | |
| 5,027,802 A | 7/1991 | Donohue | |
| 5,036,837 A | 8/1991 | Mitchell et al. | |
| 5,036,838 A | 8/1991 | Sherman | |
| 5,052,375 A | 10/1991 | Stark et al. | |
| 5,070,866 A | 12/1991 | Alexander et al. | |
| 5,078,128 A | 1/1992 | Grim et al. | |
| 5,088,481 A | 2/1992 | Darby | |
| 5,100,403 A | 3/1992 | Hotchkiss et al. | |
| 5,102,411 A | 4/1992 | Hotchkiss et al. | |
| 5,116,359 A | 5/1992 | Moore | |
| 5,125,400 A | 6/1992 | Johnson, Jr. | |
| 5,135,470 A | 8/1992 | Reeves | |
| 5,139,475 A | 8/1992 | Robicsek | |
| 5,141,489 A | 8/1992 | Sereboff | |
| 5,156,589 A | 10/1992 | Langen et al. | |
| 5,163,451 A | 11/1992 | Grellas | |
| 5,167,612 A | 12/1992 | Bonutti | |
| 5,171,296 A * | 12/1992 | Herman | 602/5 |
| 5,191,903 A | 3/1993 | Donohue | |
| 5,197,942 A | 3/1993 | Brady | |
| 5,201,702 A | 4/1993 | Mars | |
| 5,201,772 A | 4/1993 | Maxwell | |
| 5,203,321 A | 4/1993 | Donovan et al. | |
| 5,205,813 A | 4/1993 | Schmidt | |
| 5,211,161 A | 5/1993 | Stef | |
| 5,213,094 A | 5/1993 | Bonutti | |
| 5,213,095 A | 5/1993 | Dague | |
| 5,218,954 A | 6/1993 | van Bemmelen | |
| 5,226,245 A | 7/1993 | Lamont | |
| 5,232,435 A | 8/1993 | Leibinsohn | |
| 5,252,101 A | 10/1993 | Rosenwinkel et al. | |
| 5,252,102 A | 10/1993 | Singer et al. | |
| 5,261,125 A | 11/1993 | Cartwright et al. | |
| 5,277,695 A | 1/1994 | Johnson, Jr. et al. | |
| 5,285,773 A | 2/1994 | Bonutti et al. | |
| 5,297,540 A | 3/1994 | Kaiser et al. | |
| 5,312,322 A | 5/1994 | Santana | |
| 5,316,022 A | 5/1994 | Schiek, Sr. | |
| 5,323,435 A | 6/1994 | Baversten | |
| RE34,661 E | 7/1994 | Grim | |
| 5,327,882 A | 7/1994 | Saringer et al. | |
| 5,328,448 A | 7/1994 | Gray, Sr. | |
| 5,329,705 A | 7/1994 | Grim et al. | |
| 5,348,530 A | 9/1994 | Grim et al. | |
| 5,349,956 A | 9/1994 | Bonutti | |
| 5,352,216 A | 10/1994 | Shiono et al. | |
| 5,354,260 A | 10/1994 | Cook | |
| 5,364,323 A | 11/1994 | Liu | |
| 5,365,947 A | 11/1994 | Bonutti | |
| 5,370,133 A | 12/1994 | Darby et al. | |
| 5,372,597 A | 12/1994 | Hotchkiss et al. | |
| 5,376,091 A | 12/1994 | Hotchkiss et al. | |
| 5,378,223 A | 1/1995 | Grim et al. | |
| 5,382,226 A | 1/1995 | Graham | |
| 5,385,536 A | 1/1995 | Burkhead et al. | |
| 5,389,065 A | 2/1995 | Johnson, Jr. | |
| 5,391,132 A | 2/1995 | Greenwald | |
| 5,395,303 A | 3/1995 | Bonutti et al. | |
| 5,399,152 A | 3/1995 | Habermeyer et al. | |
| 5,403,265 A | 4/1995 | Berguer et al. | |
| 5,407,420 A | 4/1995 | Bastyr et al. | |
| 5,407,422 A | 4/1995 | Matthijs et al. | |

| | | | | | | |
|---|---|---|---|---|---|---|
| 5,417,643 | A | 5/1995 | Taylor | 6,296,595 | B1 | 10/2001 | Stark et al. |
| 5,419,757 | A | 5/1995 | Daneshvar | 6,371,123 | B1 | 4/2002 | Stark et al. |
| 5,421,874 | A | 6/1995 | Pearce | 6,384,755 | B1 | 5/2002 | Hayden |
| 5,435,009 | A | 7/1995 | Schild et al. | 6,409,691 | B1 | 6/2002 | Dakin et al. |
| 5,437,611 | A | 8/1995 | Stern | 6,436,058 | B1 | 8/2002 | Krahner et al. |
| 5,452,205 | A | 9/1995 | Telepko | 6,468,240 | B1 | 10/2002 | Saunders |
| 5,453,075 | A | 9/1995 | Bonutti et al. | 6,485,447 | B1 | 11/2002 | Lavery et al. |
| 5,453,082 | A | 9/1995 | Lamont | 6,491,694 | B1 | 12/2002 | Orsak |
| 5,456,268 | A | 10/1995 | Bonutti | 6,502,577 | B1 | 1/2003 | Bonutti |
| 5,456,286 | A | 10/1995 | Warner et al. | 6,503,213 | B2 | 1/2003 | Bonutti |
| 5,464,385 | A | 11/1995 | Grim | 6,506,172 | B1 | 1/2003 | Hepburn et al. |
| 5,466,213 | A | 11/1995 | Hogan et al. | 6,506,174 | B1 | 1/2003 | Saunders et al. |
| 5,466,250 | A | 11/1995 | Johnson, Jr. et al. | 6,509,659 | B1 | 1/2003 | Carroll et al. |
| 5,472,407 | A | 12/1995 | Schenck | 6,572,571 | B2 | 6/2003 | Lowe |
| 5,492,133 | A | 2/1996 | McVicker | 6,575,926 | B2 | 6/2003 | Bonutti |
| 5,503,619 | A | 4/1996 | Bonutti | 6,599,255 | B2 | 7/2003 | Zhang |
| 5,503,622 | A | 4/1996 | Wehr | 6,599,263 | B1 | 7/2003 | Bonutti et al. |
| 5,503,908 | A | 4/1996 | Faass | 6,637,429 | B2 | 10/2003 | Mundrick et al. |
| 5,518,009 | A | 5/1996 | Ruiz-Gonzalez | 6,682,497 | B2 | 1/2004 | Jensen et al. |
| 5,520,181 | A | 5/1996 | Kreidler et al. | 6,743,187 | B2 | 6/2004 | Solomon |
| 5,520,628 | A | 5/1996 | Wehr | 6,770,047 | B2 | 8/2004 | Bonutti |
| 5,527,269 | A | 6/1996 | Reithofer | 6,890,285 | B2 | 5/2005 | Rahman et al. |
| 5,531,669 | A * | 7/1996 | Varnau ............... 602/18 | 6,899,690 | B2 | 5/2005 | Saunders et al. |
| 5,535,274 | A | 7/1996 | Braitberg et al. | 6,921,377 | B2 | 7/2005 | Bonutti |
| 5,538,486 | A | 7/1996 | France et al. | 6,929,616 | B2 | 8/2005 | Bonutti et al. |
| 5,571,077 | A | 11/1996 | Klearman et al. | 6,958,048 | B2 | 10/2005 | Bonutti |
| 5,577,998 | A | 11/1996 | Johnson, Jr. et al. | 6,974,431 | B2 | 12/2005 | Jensen |
| 5,605,535 | A | 2/1997 | Lepage | 7,101,347 | B2 | 9/2006 | Culhane et al. |
| 5,609,570 | A | 3/1997 | Lamont | 7,108,671 | B2 | 9/2006 | Saunders et al. |
| 5,611,764 | A | 3/1997 | Bonutti et al. | 7,112,179 | B2 | 9/2006 | Bonutti et al. |
| 5,620,411 | A | 4/1997 | Schumann et al. | 7,182,738 | B2 | 2/2007 | Bonutti et al. |
| 5,626,537 | A | 5/1997 | Danyo et al. | 7,189,214 | B1 | 3/2007 | Saunders |
| 5,647,378 | A | 7/1997 | Farnum | 7,204,814 | B2 | 4/2007 | Peles |
| 5,653,680 | A | 8/1997 | Cruz | 7,306,573 | B2 | 12/2007 | Bonutti |
| 5,665,059 | A | 9/1997 | Klearman et al. | 7,404,804 | B2 | 7/2008 | Bonutti |
| 5,681,269 | A | 10/1997 | Basaj et al. | 2001/0047209 | A1 | 11/2001 | Solomon |
| 5,685,830 | A | 11/1997 | Bonutti | 2002/0029784 | A1 | 3/2002 | Stark |
| 5,697,894 | A | 12/1997 | Gullichsen et al. | 2002/0183655 | A1 | 12/2002 | Zhang |
| 5,713,841 | A | 2/1998 | Graham | 2003/0120183 | A1 | 6/2003 | Simmons |
| 5,755,679 | A | 5/1998 | Selner et al. | 2004/0153010 | A1 | 8/2004 | Bonutti |
| 5,761,834 | A | 6/1998 | Grim et al. | 2004/0215120 | A1 | 10/2004 | Jensen |
| 5,772,619 | A | 6/1998 | Corbett | 2005/0050152 | A1 | 3/2005 | Penner et al. |
| 5,778,565 | A | 7/1998 | Holt et al. | 2006/0036205 | A1 | 2/2006 | Bonutti |
| 5,788,659 | A | 8/1998 | Haas | 2006/0217647 | A1 | 9/2006 | Rogachevsky |
| 5,792,084 | A | 8/1998 | Wilson et al. | 2007/0038161 | A1 | 2/2007 | Bonutti et al. |
| 5,820,577 | A | 10/1998 | Taylor | 2007/0055190 | A1 | 3/2007 | Bonutti et al. |
| 5,823,975 | A | 10/1998 | Stark et al. | 2007/0100267 | A1 | 5/2007 | Bonutti et al. |
| 5,833,639 | A | 11/1998 | Nunes et al. | 2007/0135738 | A1 | 6/2007 | Bonutti et al. |
| 5,839,139 | A | 11/1998 | Fink | 2007/0197605 | A1 | 8/2007 | Glombik et al. |
| 5,848,979 | A | 12/1998 | Bonutti et al. | 2007/0219475 | A1 | 9/2007 | Bonutti et al. |
| 5,865,773 | A | 2/1999 | Koledin | 2007/0219476 | A1 | 9/2007 | Bonutti et al. |
| 5,882,320 | A | 3/1999 | Peterson | 2008/0091132 | A1 | 4/2008 | Bonutti |
| 5,882,323 | A | 3/1999 | Belkin | | | | |
| 5,919,148 | A | 7/1999 | Marko et al. | | | | |

FOREIGN PATENT DOCUMENTS

| | | |
|---|---|---|
| CA | 2065669 | 10/1993 |
| DE | 405327 | 10/1924 |
| DE | 2829562 | 1/1980 |
| DE | 8806231.7 | 5/1988 |
| EP | 0181668 | 5/1986 |
| EP | 0181688 | 5/1986 |
| EP | 0380060 | 1/1990 |
| EP | 0510840 | 10/1992 |
| FR | 2661333 | 4/1990 |
| JP | 4261657 | 9/1992 |
| JP | 2001 087296 | 4/2001 |
| RU | 1426580 | 9/1988 |
| SU | 1158195 | 5/1985 |
| SU | 1671296 | 8/1991 |
| WO | WO 88/04543 | 6/1988 |
| WO | WO 2004/073143 | 1/2004 |
| WO | WO 2005/086741 | 9/2005 |
| WO | WO 2007/051168 | 5/2007 |
| WO | WO 2007/109638 | 9/2007 |
| WO | WO 2008/036895 | 8/2008 |

OTHER PUBLICATIONS

Advertising materials from the Internet on Jun. 5, 1998 entitled: "Make DonJoy's Quadrant Your First Choice for Effective Post- Operative Shoulder Treatment". "Quadrant Brace Specifications".

Advertising materials from the Internet on Jun. 5, 1998 entitled: "Ultraslingtm by DonJoy".

Neporent et al. "Weight Training for Dummies" 1997, p. 294.

Dynasplint Systems Inc., "Practitioner Information for Dynasplint LPS Orthosis—Knee Extension", date known but prior to Aug. 23, 1991.

Publication by UE Tech, Technology Meeting Human Needs, Rehabilitation Product Catalog, vol. 7, publication date unknown, but prior to Oct. 13, 1998.

Taber's Cyclopedic Medical Dictionary 16th Edition (1989) (#34), p. 521, definition of "distraction".

Joint Active Sytems, Inc., JAS; The Proven Approach to Restoring ROM (online), Copyright 2004 www.jointactivesystems.com.

* cited by examiner

ORTHOSIS AND METHOD FOR CERVICAL MOBILIZATION

CROSS-REFERENCE TO RELATED APPLICATIONS

This Application is a continuation of U.S. patent application Ser. No. 10/909,584, filed Aug. 2, 2004 U.S. Pat. No. 7,306,573, which is a continuation of U.S. patent application Ser. No. 10/329,866, filed Dec. 26, 2002 (now U.S. Pat. No. 6,770,047), which is a continuation of U.S. patent application Ser. No. 09/728,106, filed Dec. 1, 2000 (now U.S. Pat. No. 6,503,213 B2). The entire content of each of these applications is expressly incorporated herein by reference thereto.

FIELD OF THE INVENTION

The present invention relates to a new and improved method of using a neck brace.

BACKGROUND OF THE INVENTION

A known neck brace for stabilizing a neck of a person is disclosed in U.S. Pat. No. 4,793,334. The neck brace disclosed in this patent includes a framework and straps for securing the framework to the body. A chin support member is positioned relative to the framework to present movement of the neck. The chin support member is supported on a strut. The strut is releasably and pivotally mounted to the framework. A brace member extending from the strut provides pivotable movement of the strut.

SUMMARY OF THE INVENTION

The present invention provides a novel method for using a neck brace to move a neck of a person or stabilize the neck. The method includes connecting a vest of the neck brace to a torso of the person. A support member of the neck brace is connected to the vest. A chin support of the neck brace is connected to a chin of the person. Force is applied between the support member and the chin support to move the chin support relative to the support member. A cam member guides movement of the chin support relative to the support member.

The chin support may be moved relative to the support member after the support member is connected to the torso of the person and the chin support is connected to the chin. Accordingly, upon applying force between the support member and the chin support, the chin is moved relative to the torso to move the neck of the person. The neck brace allows stretching and distraction of the neck. The neck brace can be used to stretch the neck of burn patients as well as for possible distraction of the neck for people with disc problems.

BRIEF DESCRIPTION OF THE DRAWINGS

The foregoing and other features of the invention will become more apparent upon consideration of the following description taken in connection with the accompanying drawings, wherein.

DETAILED DESCRIPTION OF THE INVENTION

Neck Brace—General Description

Figure 1:
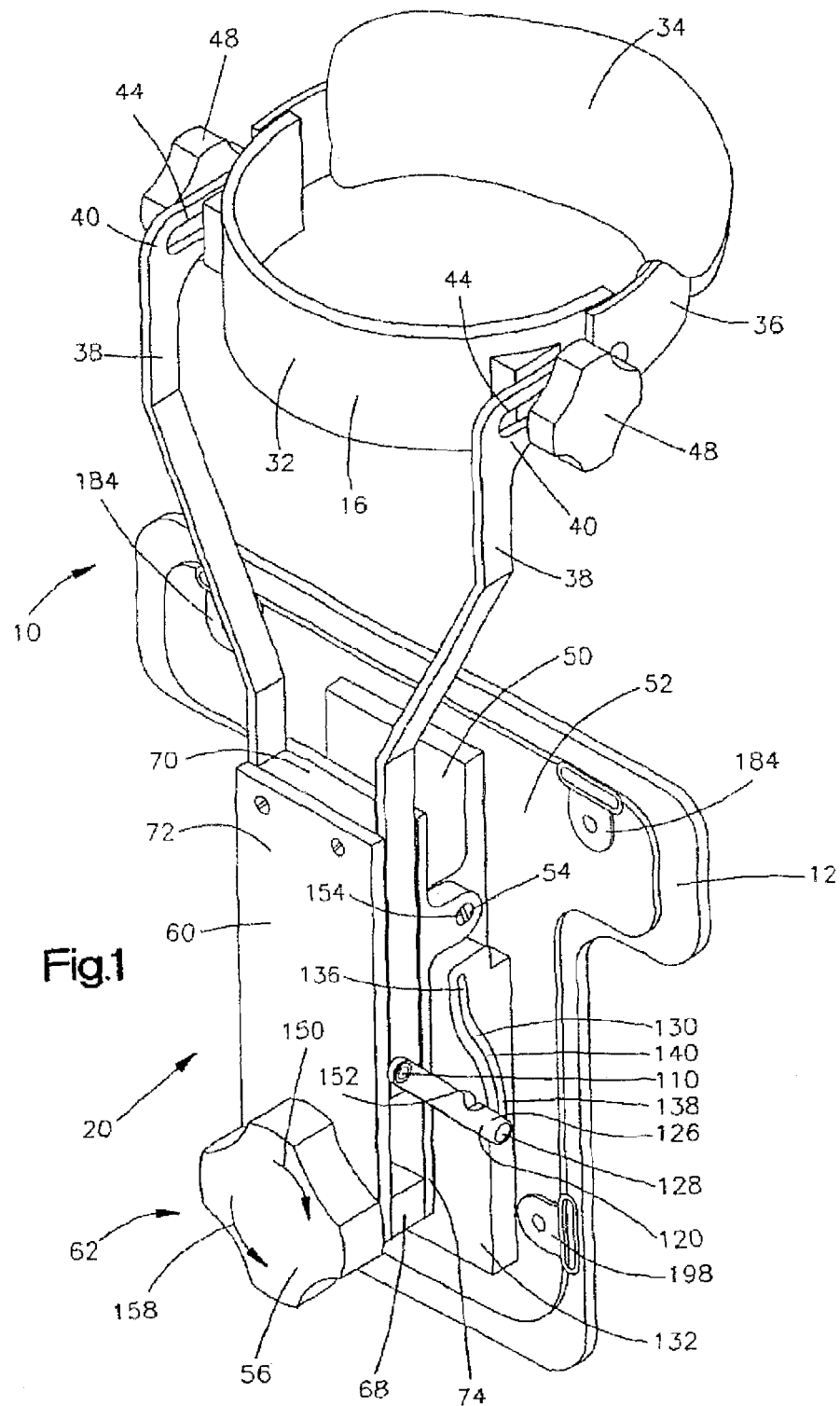
FIG. 1 is an illustration of a neck brace constructed in accordance with the present invention.

A neck brace 10 (FIGS. 1 and 1A) can be used to move or stabilize a neck 22 of a person. The neck brace 10 includes a T-shaped support member 12 which is connected with a torso 14 of a person. A chin support 16 is connected with a chin 18 of the person. An actuator mechanism 20 moves the chin support 16 relative to the support member 12. The chin support 16 is moved relative to the support member 12 after the chin support is connected to the chin 18 and the support member is connected to the torso 14 to move the neck 22 of the person. The support member 12 and the chin support 16 may have any desired construction as long as they are effective to engage the torso 14 and the chin 18.

A cloth vest 30 (FIG. 1A), which will be described in detail hereinafter, connects the support member 12 with the torso 14. The chin support 16 (FIG. 1) includes a chin portion 32 formed to engage the chin 18. A back portion 34 of the chin support 16 for engaging the back of the neck 22 is connected to the portion 32 by an elastic band 36. The elastic band 36 extends through the back portion 34 and has opposite ends connected to the chin portion 32. Accordingly, the back portion 34 can move relative to the chin portion 32.

It is contemplated that the back portion 34 could be connected to the chin portion 32 in any manner that will permit adjustment of the back portion 34 relative to the chin portion and connection of the chin support 16 to the chin 18. Furthermore, it is also contemplated that the back portion 34 could have any shape which conforms to the back of a person's neck. The chin portion 32 could have any shape that conforms to the chin 18.

Figure 1A:
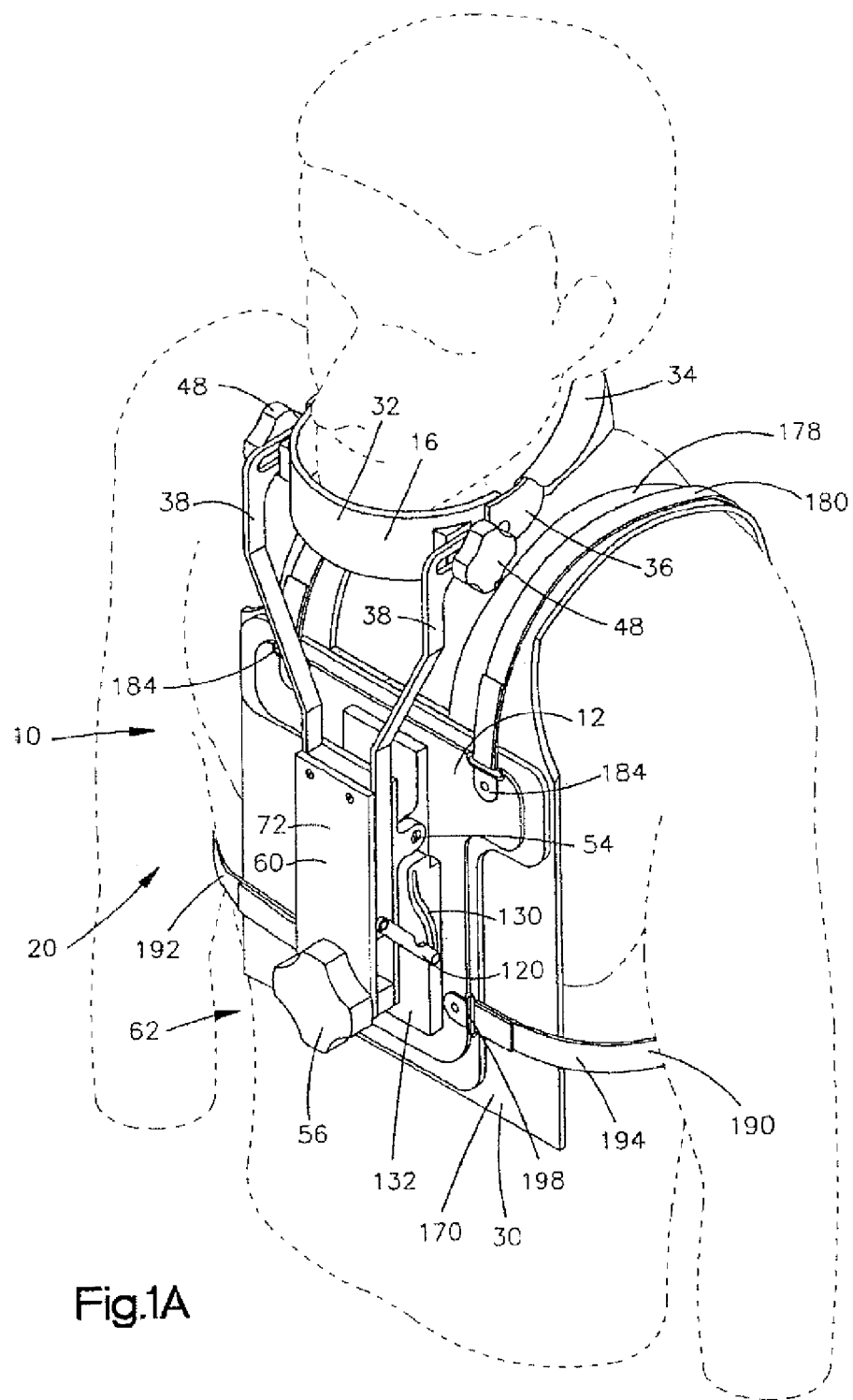
FIG. 1A is an illustration of the neck brace of FIG. 1 connected to a person.
Figure 2:
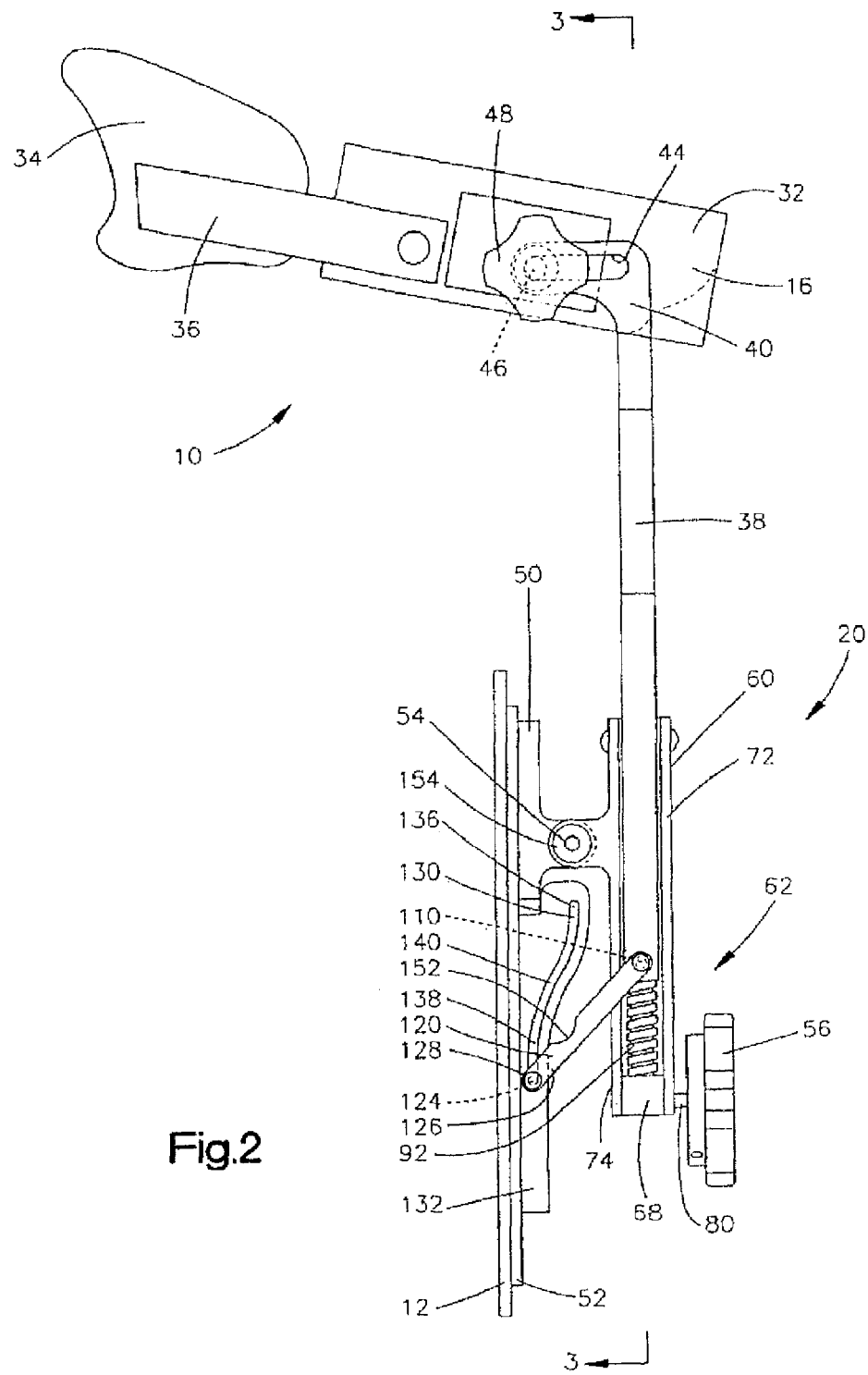
FIG. 2 is a schematic side view of a portion of the neck brace of FIG. 1.

A pair of interconnecting members or arms 38 (FIGS. 1 and 1A) connect the chin support 16 with the support member 12. The arms 38 extend from the chin support 16 to the actuator mechanism 20. Each of the arms 38 has an upper end 40 with a slot 44 (FIGS. 1 and 2). Threaded members 46 (FIG. 2) extend from the portion 32 of the chin support 16 through the slots 44. Clamping members 48 threadably engage the threaded members 46 to clamp the ends 40 of the arms 38 to the portion 32. The portion 32 can be positioned relative to the arms 38 when the clamping members 46 are loosened from the threaded members 46. The portion 32 can be pivoted about the threaded members 46 and the threaded members can be moved between the ends of the slots 44 to position the chin support 16 relative to the arms 38.

The actuator mechanism 20 (FIGS. 1 and 2) is connected to a pivot support 50 connected to a support plate 52 of the support member 12. The actuator mechanism 20 is connected to the pivot support by a pivot connection 54. The actuator mechanism 20 transmits force between the support member 12 and the chin support 16 to simultaneously pivot the actuator mechanism about a pivot axis of the pivot connection 54 and move the interconnecting members 38 relative to the actuator mechanism.

The actuator mechanism 20 transmits force from an input member which in the illustrated embodiment of the neck brace 10, is a manually rotatable knob 56. Force is transmitted from the knob 56 through the actuator mechanism 20 to the chin support 16. Force is transmitted from the actuator mechanism 20 to pivot the actuators mechanism about the pivot connection 54. In addition, force is transmitted from the knob 56 to move the interconnecting members 38 and the chin support 16 relative to the actuator mechanism 20 as the actuator mechanism pivots about the pivot connection 54.

Figure 3:
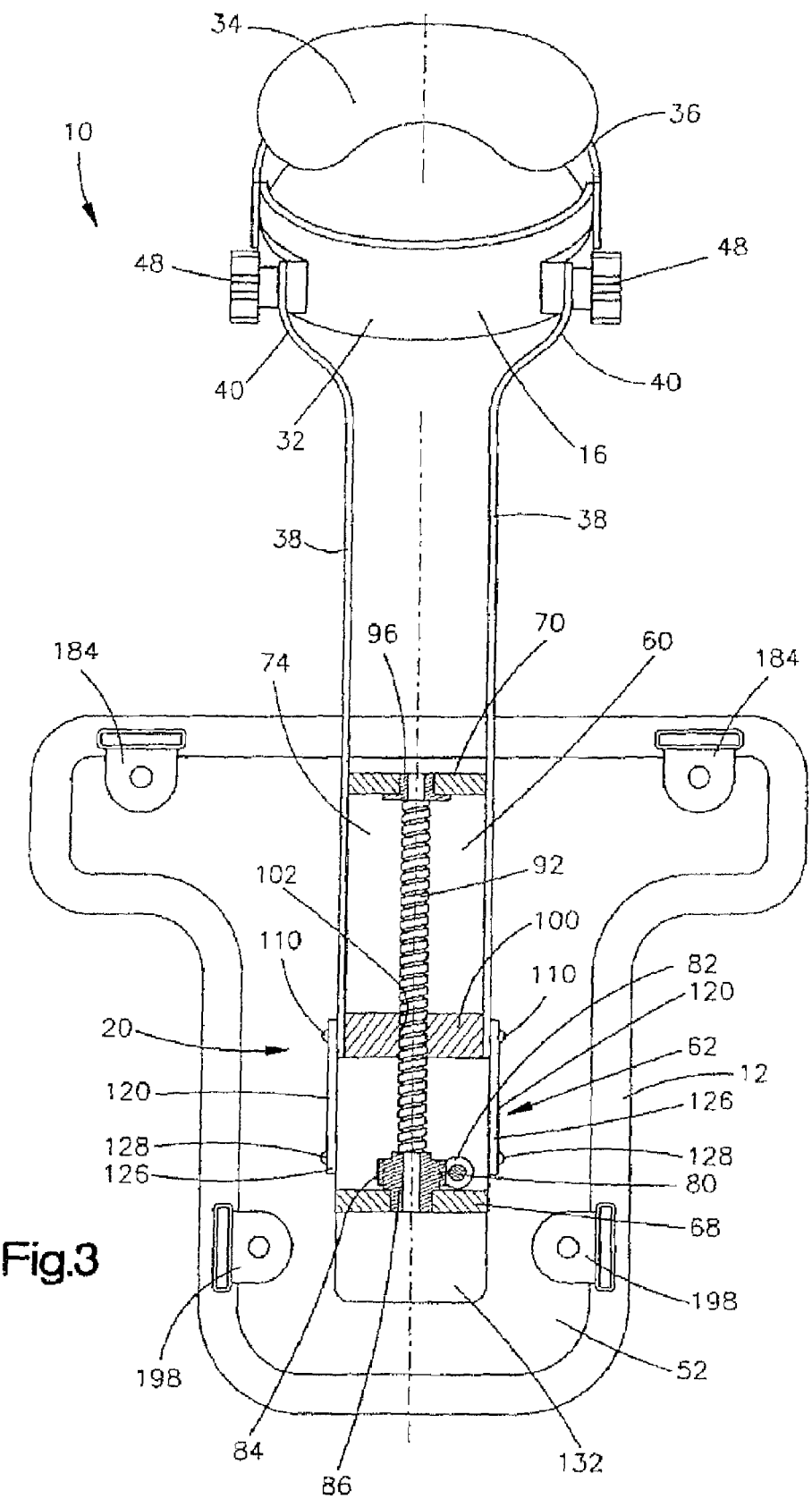
FIG. 3 is an enlarged sectional view of the neck brace taken generally along the line 3-3 in FIG. 2.

A frame 60 (FIGS. 1 and 2) of the actuator mechanism 20 has a lower housing 68 and an upper housing 70 joined by a front plate 72 and a back plate 74. The back plate 74 is connected to the pivot support 50 by the pivot connection 54. A drive mechanism 62 for the neck brace 10 is disposed substantially within the frame 60. The drive mechanism 62 includes the manually actuatable knob 56 which is fixed to a shaft 80. The shaft 80 (FIG. 3) extends into the frame 60 and a gear 82 is fixed to the shaft. The gear 82 engages external gear teeth 84 on a gear 86. Rotation of the gear 80 about its axis causes rotation of the gear 86 about its axis.

The gear 86 (FIG. 3) is fixed to an externally threaded member 92. The gear 86 is journalled for rotation in the lower housing 68. The opposite end of the screw 92 is journalled for rotation in a bushing 96 mounted in the upper housing 70 of the frame 60. A base link 100 has an internally threaded opening 102 through which the screw 92 extends in threaded engagement. As the screw 92 rotates, the base link 100 moves axially along the screw within the frame 60.

The interconnecting arms 38 (FIGS. 2 and 3) are fixedly connected to the base link 100 by screws 110. The screws 110 also fixedly connect links 120 to the base link 100 and the arms 38. The links 120 extend from the base link 100 toward the support member 12.

A pin 124 (FIG. 2) is connected to ends 126 of the links 120 by screws 128. The pin 124 extends between the ends 126 of links 120 and through a slot 130 in a cam member 132 connected with the support plate 52. The slot 130 in the cam member 132 guides movement of the pin 124 relative to the support member 12. Accordingly, the slot 130 guides movement of the base link 100, the interconnecting members 38, and the chin support 16 relative to the support member 12.

The slot 130 (FIG. 2) has a first or upper end portion 136 and a second or lower end portion 138. The upper and lower end portions 136 and 138 of the slot 130 extend in directions generally parallel to each other and the support plate 52. An intermediate portion 140 of the slot 130 extends between the end portions 136 and 138. The slot 130 guides movement of the links 120, base link 100, interconnecting members 38, and chin support 16 along paths having first and second end portions extending in directions generally parallel to each other and intermediate portions extending between the first and second end portions.

Figure 4:
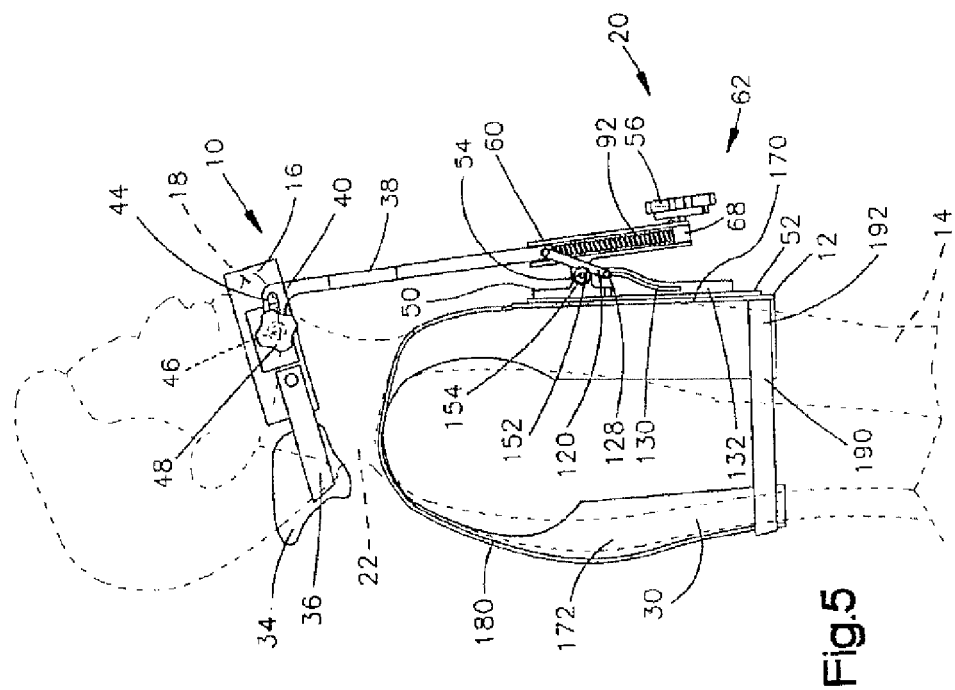
FIG. 4 is a schematic side view of the neck brace of FIG. 1 depicting the manner in which the neck brace is operated to move the neck in flexion.
Figure 5:
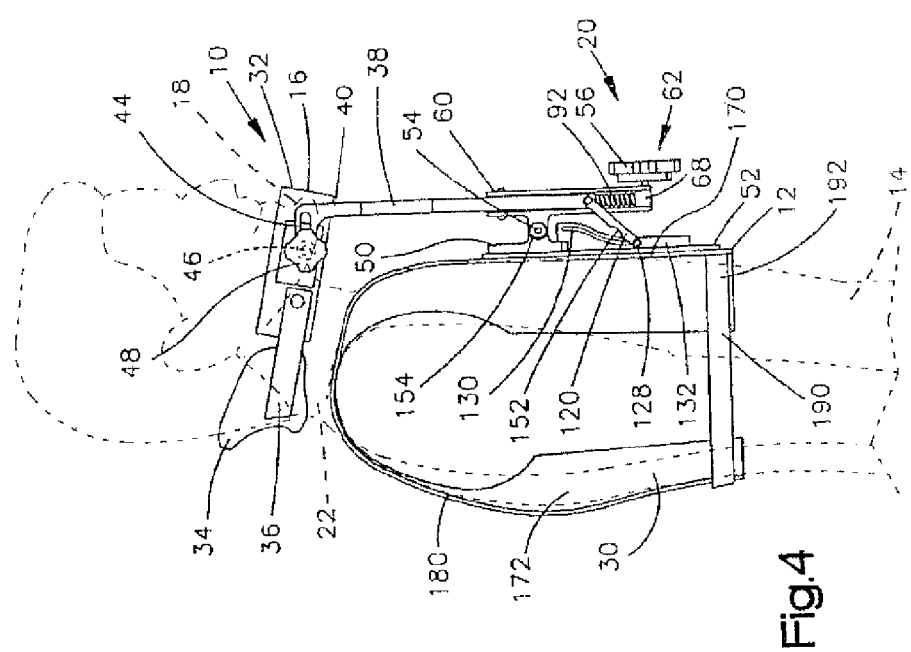
FIG. 5 is a schematic side view of the neck brace, generally similar to FIG. 4, depicting the manner in which the neck brace is operated to move the neck in extension.

The actuator mechanism 20 is operable to move the chin support 16 and the chin 18 prom an initial position, such as the one shown in FIG. 4, to actuated positions, such as the one shown in FIG. 5. Operation of the actuator mechanism 20 moves the chin support 16 along, the path having first and second end portions extending in directions generally parallel to each other and an intermediate portion extending between the first and second end portions. As this occurs, the frame 60 pivots about the pivot connection 54 and the interconnecting members 38 move relative to the frame.

Moving Neck in Extension

When the input knob 56 is manually rotated in the direction of arrow 150 in FIG. 1, the actuator mechanism 20 is operated. Operation of the actuator mechanism 20 transmits force from the knob 56 to the base link 100. The base link 100 and arms 38 move in an upward direction as view in FIG. 4 from the orientation shown in FIG. 4 toward the orientation shown in FIG. 5 to move the neck 22 in extension.

Operation of the actuator mechanism 20 moves the base link 100 and the interconnecting members 38 away from the lower housing 68. As the base link 100 moves away from the lower housing 68, the links 120 move with the base link. Accordingly, the pin 124 moves along the slot 130 from the lower end portion 138 to the intermediate portion 140 and to the upper end portion 136. As the pin 124 moves along the slot 130, the frame 60 pivots in a counterclockwise direction (as viewed in FIGS. 4 and 5) about the pivot connection 54. Simultaneously therewith, the interconnecting members 38 move relative to the frame 60. Pivotal movement of the frame 60 causes the chin support 16, the interconnecting members 38, and the base link 100 to move about the pivot axis of the pivot connection 54. As the interconnecting members 38 move relative to the frame 60 and the frame pivots about the pivot connection 54 toward the orientation shown in FIG. 5, the neck 22 is moved in extension.

During movement of the interconnecting members 38 relative to the frame 60 and movement of the neck 22 in extension, the actuator mechanism 20 transmits force to the chin support 16. The interconnecting members 38 move relative to the frame 60 and the frame pivots about the pivot connection 54. In the illustrated embodiment of the invention, the interconnecting members 38 and the frame 60 are moved by the actuator mechanism 20 through a range of movement from the positions shown in FIG. 4 to a condition of maximum extension as shown in FIG. 5. When the links 120 are in the positions showing in FIG. 5, notches 152 in the links 120 extend around screws 154 of the pivot connection 54. It should be understood that the foregoing specific range of movement of the neck brace 10 has been set forth herein for purposes of clarity of description and that it is contemplated that specific embodiments of the neck brace will have interconnecting members 38 and a frame 60 which move through different distances relative to each other and are movable to different angular orientations relative to the support member 12.

It is contemplated that the specific procedure which is followed to move the neck 22 in extension will vary depending upon the conditions of the neck and the desires of a surgeon or therapist supervising the use of the neck brace 10. However, it is believed that it may be preferred to use a static progressive stretch procedure during movement of the neck 22. This procedure is implemented by operating the actuator mechanism 20 to move the neck 22 in extension to a limit of tolerance of the neck without severe pain. This position of the neck 22 is held for a period of time, for example, five minutes, to allow the tissue of the neck to relax. As the tissue relaxes, stress decreases. After the period of time has elapsed, the input member is manually rotated to again stretch the tissue of the neck 22 to the limit of tolerance. This condition is again held for a period of time, for example, five minutes, to allow the tissue in the neck 22 to again relax. The process is repeated for the duration of a therapy session which, may be approximately 30 minutes long.

The input knob 56 may be manually rotated by either the patient, that is, the person having the neck 22 on which the neck brace 10 is mounted, or by a supervisory personnel, such as a therapist. However, it is believed that it will be desired to have the patient actuate the neck brace 10 to affect movement of the neck 22. The patient can feel when the tissue has tightened and the neck 22 has been moved to the limit of its tolerance, without severe pain. The patient can also feel when the tissue has relaxed and further actuation of the neck brace 10 to further move the neck 22 in extension can be undertaken.

Moving Neck in Flexion

When the neck 22 is to be moved in flexion, the input knob 56 is manually rotated, in the direction of arrow 158 in FIG. 1, to operate the actuator mechanism 20. Operation of the actuator mechanism 20 transmits force from the input knob 56 to the base link 100. As the input knob 56 is manually rotated, the actuator mechanism 20 moves the base link 100 toward the lower housing 68 and away from the tipper housing 70. Thus, the links 120 are moved from the position shown in FIG. 5 toward the position shown in FIG. 4 as the input knob 56 is manually rotated.

As the base link 100 is moved toward the lower housing 68, the links 120 move downward, as viewed in FIG. 5. As the links 120 move downward, the pin 124 moves along the slot 130 from the upper end portion 136 through the interconnecting portion 140 to the lower end portion 138. Thus, the interconnecting members 38 move relative to the frame 60 and the frame pivots in a clockwise direction (as viewed in FIG. 5) about the pivot connection 54. As the interconnecting members 38 move and the frame 60 pivots, the neck 22 is moved in fe ion from the initial condition shown in FIG. 5 toward the condition shown in FIG. 4.

As the interconnecting members 38 move relative to the frame 60 and the frame pivots about the pivot connection 54, the chin support 16 and the chin 18 are moved from the position shown in FIG. 5 toward the position shown in FIG. 4. Thus, force is transmitted from the actuator mechanism 20 to the interconnecting members 38 to move the chin support 16 along a path having first and second end portions extending in directions generally parallel to each other and an intermediate portion extending between the first and second end portions.

It is believed that a static progressive stretch procedure may be preferred for moving the neck 22 in flexion. Thus, the input knob 56 is manually rotated to operate the actuator mechanism 20 and affect movement of the chin support 16 to move the neck 22 in flexion until the patient feels tissue tightness, but not severe pain. The neck brace 10 is maintained in that position for a period of time, which may be five minutes. When the tissue relaxes, the input knob 56 is again rotated to stretch the tissue. The steps of operating the neck brace 10 to stretch the tissue, interrupting operation of the neck brace to allow the tissue to relax and then again operating the neck brace to again stretch the tissue is repeated for the duration of a therapy session.

As was previously mentioned, the knob 56 may be manually rotated by a therapist or surgeon. However, it is believed that it will be preferred to have the patient manually rotate the knob. Thus, the person having the neck 22 will rotate the knob 56 until he or she feels the tissue tighten and will further rotate the knob to further move the neck when he or she feels the tissue relax.

In the example of moving the neck 22 in flexion, illustrated in FIGS. 4 and 5, the neck is moved from an initial condition illustrated in FIG. 5. However, it is believed, that under certain circumstances, the neck may initially be in a condition between the conditions shown in FIGS. 4 and 5 and moved in flexion to the condition in FIG. 4. When this is to be done, the neck brace 10 is operated to move the neck 22 in flexion toward the condition illustrated in FIG. 4.

Stabilizing Neck

The neck brace 10 can be used to stabilize the neck 22 in a desired position. When the neck brace 10 is to be used to stabilize the neck 22, the vest 30 is connected with the torso 14. The support member 12 is placed over the chest and connected with the vest 30. The actuator mechanism 20 is operated by turning the knob 56 in the direction of arrow 150 or arrow 158 to move the interconnecting members 38 relative to the support member 12.

Operation of the actuator mechanism 20 transmits force from the input knob 56 to the base link 100. As the input knob 56 is rotated, the base link 100, the links 120, and tile interconnecting members 38 move relative to the frame 60. The pin 124 moves along the slot 130. Accordingly, the interconnecting members 38 move along paths having first and second end portions extending in directions generally parallel to each other and intermediate portions extending between the first and second end portions. The interconnecting members 38 move relative to the flame 60 and the frame pivots about the pivot connection 54.

When the interconnecting members 38 have been moved to a desired position, the chin support 16 is connected with the chin 18. The chin support 16 is positioned relative to the interconnecting members 38. The clamping members 48 are threaded onto the threaded members 46 to clamp the interconnecting members 38 to the chin support 16. Once the neck brace 10 is connected to the person, operation of the actuator mechanism 20 is prevented so that the neck 22 is stabilized.

Actuator Mechanism

The actuator mechanism 20 (FIGS. 2 and 3) is supported on the pivot support 50 of the support member 12. The actuator mechanism 20 includes the externally threaded member 92 which is rotatably supported within the frame 60. A central axis of the screw 92 extends through the center of the base link 100.

The manually rotatable knob 56 is fixedly connected to the shaft 80. The shaft 80 (FIG. 3) has the gear 82 in meshing engagement with the gear 84 connected with the screw 92. The base link 100 has internal thread convolutions which engage with external thread convolutions on the screw 92. In the illustrated embodiment of the invention, the base link 100 is movable relative to the frame 60 and the screw 92. However, the frame 60 and the screw 92 could be movable relative to the base link 100. If this was done, the base link 100 would be connected with the support member 12 and the frame 60 would be connected with the interconnecting members 38.

Upon rotation of the input member or knob 56, the base link 100 moves relative to the screw 92 and the frame 60. As this occurs, the links 120 move with the base link 100 relative to the frame 60. Also, the interconnecting members 38 and the chin support 16 move relative to the frame 60 and the frame pivots about the pivot connection 54. Of course, movement of the interconnecting members 38 and the frame 60 moves the neck 22 with which the neck brace 10 is connected. Movement of the base link 100 toward the upper housing 70 moves the neck in extension. Movement of the base link 100 away from the upper housing 70 moves the neck 22 in flexion.

The base link 100 and the frame 60 can be moved from an initial condition between the conditions shown in FIGS. 4 and 5 to one of the actuated conditions shown in FIGS. 4 and 5. The base link 100 and the interconnecting members 38 move along paths having first and second end portions extending in directions generally parallel to each other and interconnecting portions extending between the first and second end portions. The base link 100 and the interconnecting members 38 are guided along the paths due to engagement of the pill 124 in the slot 130 of the cam member 132.

In the illustrated embodiment of the invention, the screw 92 has a thread so that the knob 56 is manually rotated in a clockwise direction, as indicated by arrow 150 in FIG. 1, to move the base link 100 toward the upper housing 70. When the knob 56 is manually rotated in a counterclockwise direction, the base link 100 moves away from the upper housing 70. It should be understood that an input member other than the knob 56 could be used to operate the actuator mechanism 20 if desired.

Vest

Figure 6:
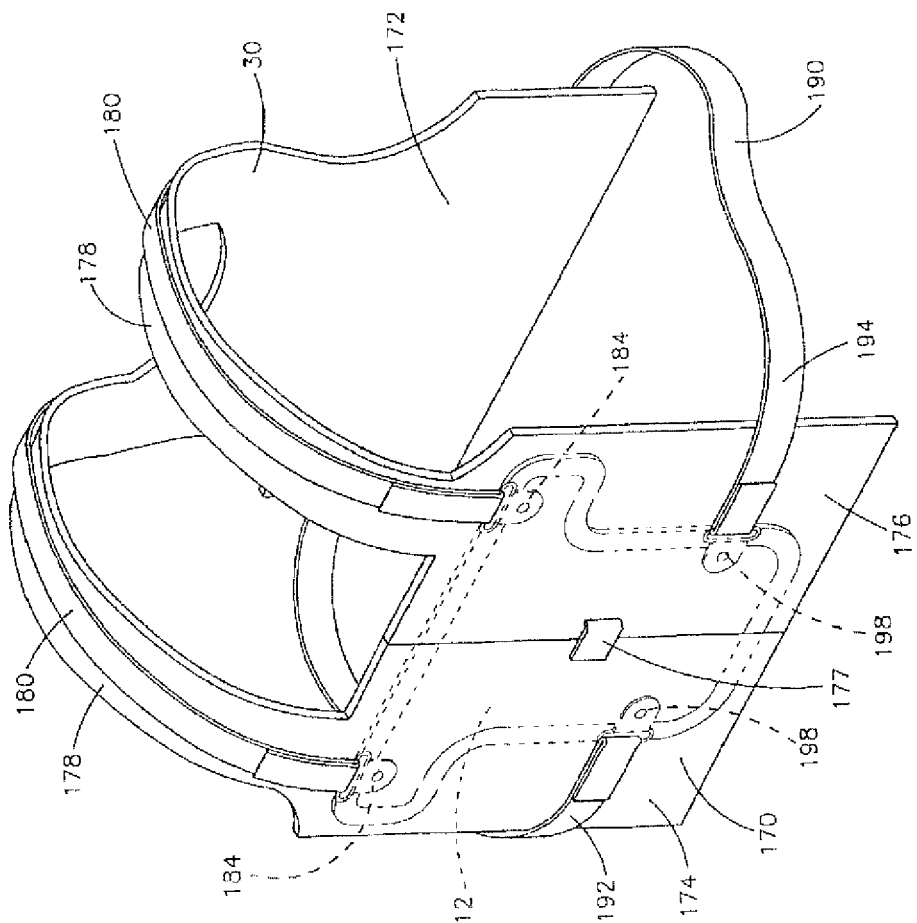
FIG. 6 is an illustration of a vest of the neck brace of FIG. 1.

The support member 12 (FIGS. 1A and 6) is connected with the torso 14 of the person using the, vest 30. The vest 30 (FIG. 6) has a front portion 170 and a back portion 172. The front portion 170 has side portions 174 and 176. A catch member 177 is fixedly connected to the side portion 174 and is releasably connected to the side portion 176 to bold the side portions together when the vest 30 is worn. Shoulder portions 178 interconnect the front portion 170 and the back portion 172.

The shoulder portions 178 extend over the shoulders or the person when the vest 30 is connected to the torso 14. The front portion 170 covers the chest of the person. The back portion 172 covers the back of the person when the person is wearing the vest 30.

Shoulder straps 180 (FIGS. 1A and 6) are connected with the back portion 172 and extend over the shoulder portions 178 to connect the vest 30 to the person. The straps 180 also connect the support member 12 to the vest 30. The straps 180 extend through retainers 184 connected to the support member 12 to secure the support member to the vest 30.

A suitable strap 190 (FIGS. 1A and 6) extends around a mid-section of the person and through loops (not shown) on the back portion 172 of the vest 30. The strap 190 has opposite end portions 192 and 194. The end portions 192 and 194 of the strap 190 extend through retainers 198 connected with the support member 12 to further connect the support member to the vest 30 and the vest to the person.

Conclusion

The present invention provides a new and improved method for using a neck brace 10. The neck brace 10 can be used to stabilize the neck 22 or to move the neck in extension or flexion. The support member 12 is connected with a torso 14 of the person and a chin support 16 is connected with a chin 18 of the person. An actuator mechanism 20 is operated to move the chin support 16 relative to the support member 12. The chin support 16 is guided along a path by the pin 124 extending into the slot 130 of the cam member 132.

From the above description of the invention, those skilled in the art will perceive improvements, changes and modifications. Such improvements, changes and modifications within the skill of the art are intended to be covered by the appended claims.

What is claimed is:

1. A device for treating a spine of a patient, comprising:
    a support member configured to be connected to a torso of a patient;
    a neck support for engaging at least a portion of a neck of the patient;
    an actuator mechanism for distracting a spine of the patient relative to the torso by moving the neck support relative to the support member; and
    a control operatively connected to said actuator mechanism to adjust distraction of the spine,
    wherein said actuator mechanism is operable by the patient.

2. The device according to claim 1, wherein said control includes at least one knob rotatably mounted to said actuator mechanism.

3. The device according to claim 1, wherein said actuator mechanism includes at least one gear connected to said control, said at least one gear operative to distract the spine when said control is actuated.

4. The device according to claim 1, wherein said control is adjustable when said device is worn by the patient and said control is operable based on patient feedback.

5. The device according to claim 1, wherein said actuator mechanism moves the spine with a composite force, the composite force having a first component and a second component orthogonal to the first component.

6. The device according to claim 5, wherein at least a portion of said actuator mechanism is extendable in a generally superior direction relative to said support member; and wherein said actuator mechanism is tiltable forward and backward about an axis aligned substantially in a medial-lateral orientation.

7. The device according to claim 1, wherein said neck support includes a chin support for engaging at least a portion of a chin of the patient, said chin support operatively connected to and moved by said actuator mechanism.

8. The device according to claim 1, wherein said actuator mechanism is selectively actuatable to flex and extend the neck of the patient.

9. The device according to claim 1, wherein said actuator mechanism is movable to a first position, said first position stretching the neck of the patient, and is movable to a second position, said second position further stretching the neck of the patient.

10. The device according to claim 1, wherein said neck support includes a back portion configured to engage the neck of the patient proximate a base of a skull of the patient.

11. The device according to claim 10, wherein a strap secures said back portion adjacent to the neck.

12. The device according to claim 1, wherein said support member is configured to engage a shoulder of the patient.

13. A device for treating a spine of a patient, comprising:
    a torso support configured to engage a torso of a patient;
    a back portion configured to engage at least a portion of a neck of the patient;
    an actuator mechanism mounted to said torso support;
    at least one arm operatively connecting said actuator mechanism and said back portion; and
    a knob connected to said actuator mechanism to adjust distraction of a spine of the patient.

14. The device of claim 13, wherein said actuator mechanism includes at least one gear configured to adjust a distance between said torso support and said back portion upon rotation of said knob.

15. The device of claim 14, wherein said actuator mechanism includes a shaft interposing said knob and said at least one gear.

16. The device of claim 13, wherein said actuator mechanism is configured so that rotation of said knob in a first direction increases the distance between said torso support and said back portion; and wherein said actuator mechanism is configured so that rotation of said knob in a second direction decreases the distance between said torso support and said back portion.

17. The device of claim 13, wherein said actuator mechanism is pivotally mounted to said torso support.

18. The device of claim 13, wherein said actuator mechanism is operative to prevent a force applied to said at least one arm from causing rotation of said knob.

19. The device of claim 18, wherein said actuator mechanism includes a base link including an internally threaded opening engaged with a screw, said base link coupled to said at least one arm and said screw operatively coupled to said knob, said actuator mechanism thereby preventing the force applied to said at least one arm from causing rotation of said knob.

20. The device of claim 13, wherein said torso support engages a shoulder of the patient.

21. The device of claim 13, wherein said back portion is adjustably mounted to said at least one arm.

22. The device of claim 13, wherein said knob is operative to cause at least one of flexion and extension of the spine of the patient while controlling a distance between said torso support and said back portion to adjust distraction of the spine of the patient.

23. The device of claim 13, wherein said back portion is configured to articulate the neck of the patient into a slightly flexed position prior to distracting the spine of the patient.

24. A neck brace comprising:
a head support configured to engage at least one of a chin of a patient and a neck of the patient;
a torso support configured to connect to a torso of the patient;
an actuator mechanism mounted to said torso support;
at least one arm extending generally superiorly from said actuator mechanism and connected to said head support; and
a knob connected to said actuator mechanism, said knob rotatable by the patient to move said at least one arm relative to said actuator mechanism.

25. The neck brace of claim 24, wherein said head support includes at least one back portion shaped to conform to at least a portion of the neck of the patient proximate a base of a skull of the patient.

26. The neck brace of claim 25, wherein said head support extends generally posteriorly from said at least one arm to said back portion along at least one side of a head of the patient.

27. The neck brace of claim 25, wherein said head support includes a chin support shaped to conform to a chin of the patient.

28. The neck brace of claim 24, further comprising a pivot connection pivotally connecting said actuator mechanism relative to said torso support, said pivot connection oriented generally in a medial-lateral direction.

29. The neck brace of claim 24, further comprising a pin slidably positioned within a slot defined by said torso support, said pin coupling said actuator mechanism to said torso support.

30. The neck brace of claim 24, wherein said knob is operative to increase a distance between said torso support and said head support upon rotation of said knob in a first direction and operative to decrease the distance between said torso support and said head support upon rotation of said knob in a second direction, the second direction opposite the first direction.

31. The neck brace of claim 24, wherein said at least one arm includes an upper end positioned generally opposite said actuator mechanism; and wherein said head support is slidably adjustably mounted to said upper end of said at least one arm.

32. The neck brace of claim 31, further comprising at least one clamp selectively inhibiting sliding adjustment of said head support relative to said upper end of said at least one arm.

33. The neck brace of claim 24, wherein said torso support is configured to releasably engage an anterior portion of the torso of the patient.

34. The neck brace of claim 24, further comprising at least one strap configured to releasably couple said torso support to the torso of the patient.

35. The neck brace of claim 24, wherein increasing the distance between said head support and said torso support elongates at least a portion of a spine of the patient.

36. The neck brace of claim 24, wherein increasing the distance between said head support and said torso support reduces pressure in at least a portion of a spine of the patient.

37. The neck brace of claim 24, wherein increasing the distance between said head support and said torso support distracts at least a portion of a spine of the patient.

38. The neck brace of claim 24, wherein adjusting the distance between said head support and said torso support at least one of flexes and extends at least a portion of a spine of the patient.

39. The device according to claim 1, wherein said control moves said neck support relative to said actuator mechanism to distract the spine.

40. A device for treating a spine of a patient, comprising:
a support member configured to be connected to a torso of a patient;
a neck support for engaging at least a portion of a neck of the patient;
an actuator mechanism for distracting a spine of the patient relative to the torso, said actuator mechanism comprising at least one gear; and
a control operatively connected to said actuator mechanism, said control actuatable by the patient to operate said at least one gear to adjust distraction of the spine.

41. The device according to claim 40, wherein said control comprises a knob rotatably mounted to said actuator mechanism.

42. The device according to claim 41, wherein said knob is rotatable to move said back portion relative to said actuator mechanism.

43. The device according to claim 41, wherein said knob is rotatable to control a distance between said torso support and said back portion.

44. The device according to claim 41, wherein said knob is configured to resist movement between said torso support and said back portion.

45. The device according to claim 13, wherein said knob is rotatable to move said back portion relative to said actuator mechanism.

46. The device according to claim 13, wherein said knob is rotatable to control a distance between said torso support and said back portion.

47. The device according to claim 13, wherein said knob is configured to resist movement between said torso support and said back portion.

48. A device for treating a spine of a patient, comprising:
a torso support configured to engage a torso of a patient;
a back portion configured to engage at least a portion of a neck of the patient;
an actuator mechanism mounted to said torso support, said actuator mechanism comprising at least one gear;
at least one arm operatively connecting said actuator mechanism and said back portion; and
a knob rotatably connected to said actuator mechanism to adjust distraction of a spine of the patient, said knob rotatable by the patient to move said at least one gear to adjust a distance between said torso support and said back portion.

49. The device according to claim 48, wherein rotation of said knob in a first direction increases the distance between said torso support and said back portion and rotation of said knob in a second direction decreases the distance between said torso support and said back portion.

50. The device according to claim 48, wherein said actuator mechanism comprises:
a base link coupled to said at least one arm, said base link defining an internally threaded opening; and an externally threaded screw rotatably positioned with said opening and operatively coupled to said knob, said actuator mechanism thereby preventing a force applied to said at least one arm from causing rotation of said knob.

51. The device according to claim 48, wherein said knob is rotatable to cause at least one of flexion and extension of the spine of the patient while controlling the distance between said torso support and said back portion.

52. The device according to claim 48, wherein said back portion is configured to articulate the neck of the patient into a flexed position prior to distracting the spine of the patient.

53. The device according to claim 1, wherein at least a portion of the spine is progressively stretched.

54. The device according to claim 13, wherein at least a portion of the spine is progressively stretched.

55. The neck brace according to claim 24, wherein at least a portion of a spine is progressively stretched.

56. The device according to claim 40, wherein at least a portion of the spine is progressively stretched.

* * * * *